US009245338B2

(12) United States Patent
Mestha et al.

(10) Patent No.: US 9,245,338 B2
(45) Date of Patent: Jan. 26, 2016

(54) INCREASING ACCURACY OF A PHYSIOLOGICAL SIGNAL OBTAINED FROM A VIDEO OF A SUBJECT

(71) Applicant: Xerox Corporation, Norwalk, CT (US)

(72) Inventors: Lalit Keshav Mestha, Fairport, NY (US); Survi Kyal, Rochester, NY (US); Beilei Xu, Penfield, NY (US)

(73) Assignee: Xerox Corporation, Norwalk, CT (US)

( * ) Notice: Subject to any disclaimer, the term of this patent is extended or adjusted under 35 U.S.C. 154(b) by 89 days.

(21) Appl. No.: 14/281,072

(22) Filed: May 19, 2014

(65) Prior Publication Data

US 2015/0332457 A1  Nov. 19, 2015

(51) Int. Cl.
*G06T 7/00* (2006.01)
*G06K 9/00* (2006.01)
*G06K 9/20* (2006.01)

(52) U.S. Cl.
CPC ............ *G06T 7/0016* (2013.01); *G06K 9/0053* (2013.01); *G06K 9/0055* (2013.01); *G06K 9/00362* (2013.01); *G06K 9/2018* (2013.01); *G06K 2009/00939* (2013.01); *G06T 2207/10016* (2013.01); *G06T 2207/30004* (2013.01)

(58) Field of Classification Search
CPC ........... G06T 2207/20201; G06T 2207/30088; G06T 5/002; G06T 2207/10016; G06T 2207/10024
USPC ........................................................ 382/103
See application file for complete search history.

(56) References Cited

U.S. PATENT DOCUMENTS

| 3,335,716 A * | 8/1967 | Alt .................... A61B 5/015 346/33 ME |
| 8,600,213 B2 | 12/2013 | Mestha et al. |
| 2013/0215244 A1 | 8/2013 | Mestha et al. |
| 2013/0342670 A1 | 12/2013 | Kyal et al. |
| 2013/0343614 A1 * | 12/2013 | Kyal .................... G06K 9/0057 382/107 |
| 2014/0240511 A1 * | 8/2014 | Nystrom ............... H04N 5/33 348/164 |

OTHER PUBLICATIONS

Xu et al., "Compensating for Motion During Real-Time Batch Processing Of Video For Physiological Function Assessment", U.S. Appl. No. 14/211,455, filed Mar. 14, 2014.

(Continued)

*Primary Examiner* — Gregory F Cunningham
(74) *Attorney, Agent, or Firm* — Philip E. Blair; Fleit Gibbons Gutman Bongini & Bianco PL

(57) ABSTRACT

What is disclosed is a system and method for increasing the accuracy of physiological signals obtained from video of a subject being monitored for a desired physiological function. In one embodiment, image frames of a video are received. Successive batches of image frames are processed. For each batch, pixels associated with an exposed body region of the subject are isolated and processed to obtain a time-series signal. If movement occurred during capture of these image frames that is below a pre-defined threshold level then parameters of a predictive model are updated using this batch's time-series signal. Otherwise, the last updated predictive model is used to generate a predicted time-series signal for this batch. The time-series signal is fused with the predicted time-series signal to obtain a fused time-series signal. The time-series signal for each batch is processed to obtain a physiological signal for the subject corresponding to the physiological function.

25 Claims, 6 Drawing Sheets

(56) References Cited

OTHER PUBLICATIONS

Xu et al., "A Video Acquisition System And Method For Monitoring A Subject For A Desired Physiological Function", U.S. Appl. No. 13/921,939, filed Jun. 19, 2013.

Tanaka et al., "Processing Source Video For Real-Time Enhancement Of A Signal Of Interest", U.S. Appl. No. 13/745,283, filed Jan. 18, 2013.

Kyal et al., "Continuous Cardiac Signal Generation From A Video Of A Subject Being Monitored For Cardiac Function", U.S. Appl. No. 13/871,766, filed Apr. 26, 2013.

Kyal et al., "Real-Time Video Processing For Respiratory Function Analysis", U.S. Appl. No. 14/195,111, filed Mar. 3, 2014.

* cited by examiner

INCREASING ACCURACY OF A PHYSIOLOGICAL SIGNAL OBTAINED FROM A VIDEO OF A SUBJECT

TECHNICAL FIELD

The present invention is directed to systems and methods for increasing the accuracy of physiological signals obtained from a video of a subject being monitored for a desired physiological function.

BACKGROUND

Monitoring of patient cardio-respiratory events is of vital clinical importance in the early detection of potentially fatal conditions. Current technologies that involve contact sensors require that the individual wears such devices constantly. Such a requirement can lead to discomfort, psychological dependence, loss of dignity, and may even cause additional medical issues such as skin infection when sensors have to be worn for an extended period of time. Elderly patients, infants, and those suffering from chronic medical conditions are more likely to suffer from such negative effects of continuous monitoring. The use of an unobtrusive, non-contact, imaging based monitoring of physiological events can go a long way towards alleviating some of these issues. Previous efforts have been directed to systems and methods which employ video image devices for monitoring a patient for a desired physiological function. In these methods, videos are captured of a region of interest of the resting patient and processed to estimate cardiac and respiratory functions from physiological signals extracted from time-series signals obtained from those videos. Xerox researchers have determined that movement by the resting patient such as turning the head, moving an arm, and the like, may impart or induce motion artifacts into the physiological signals extracted from video of that patient and thus negatively impact the accuracy of physiological signals obtained therefrom. The present application is directed to this issue.

Accordingly, what is needed in this art are sophisticated systems and methods for increasing the accuracy of physiological signals obtained from a video of a subject being monitored for a desired physiological function.

INCORPORATED REFERENCES

The following U.S. patents, U.S. patent applications, and Publications are incorporated herein in their entirety by reference.

"A Video Acquisition System And Method For Monitoring A Subject For A Desired Physiological Function", U.S. patent application Ser. No. 13/921,939, by Xu et al.

"Processing Source Video For Real-Time Enhancement Of A Signal Of Interest", U.S. patent application Ser. No. 13/745,283, by Tanaka et al.

"Filtering Source Video Data Via Independent Component Selection", U.S. patent application Ser. No. 13/281,975, by Mestha et al.

"Removing Environment Factors From Signals Generated From Video Images Captured For Biomedical Measurements", U.S. patent application Ser. No. 13/401,207, by Mestha et al.

"Continuous Cardiac Signal Generation From A Video Of A Subject Being Monitored For Cardiac Function", U.S. patent application Ser. No. 13/871,766, by Kyal et al.

"Continuous Cardiac Pulse Rate Estimation From Multi-Channel Source Video Data With Mid-Point Stitching", U.S. patent application Ser. No. 13/871,728, by Kyal et al.

"Real-Time Video Processing For Respiratory Function Analysis", U.S. patent application Ser. No. 14/195,111, Kyal et al.

"Compensating For Motion During Real-Time Batch Processing Of Video For Physiological Function Assessment", U.S. application Ser. No. 14/211,455, by Xu et al.

BRIEF SUMMARY

What is disclosed is a system and method for increasing the accuracy of physiological signals obtained from a video of a subject being monitored for a desired physiological function. In one embodiment, the present method involves the following. First, image frames of a video of a subject being monitored for a desired physiological function are received. The video has been captured by a video imaging device. The image frames are of at least a portion of an exposed body region of the subject where a physiological signal corresponding to the desired physiological function is registered by the video imaging device. A size N of a batch of image frames is defined. Then, the following are performed on batches of image frames of size N. The batch of image frames is processed to isolate pixels associated with the exposed body region and the isolated pixels are processed to obtain a time-series signal for this batch. Thereafter, a determination is made whether a movement occurred during video acquisition of this batch of image frames. If, as a result of the determination, the movement is below a threshold level predefined for movement then the parameters of a predictive model are updated using the time-series signal obtained from this batch of image frames. Otherwise, the last updated predictive model is used to generate a predicted time-series signal for the current batch, and the time-series signal obtained for this batch is fused with the predicted time-series signal to obtain a fused time-series signal. Time-series signal obtained for batches of image frames whether fused or otherwise, are processed to obtain a physiological signal which corresponds to the physiological function for which the subject is being monitored.

Features and advantages of the above-described system and method will become apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
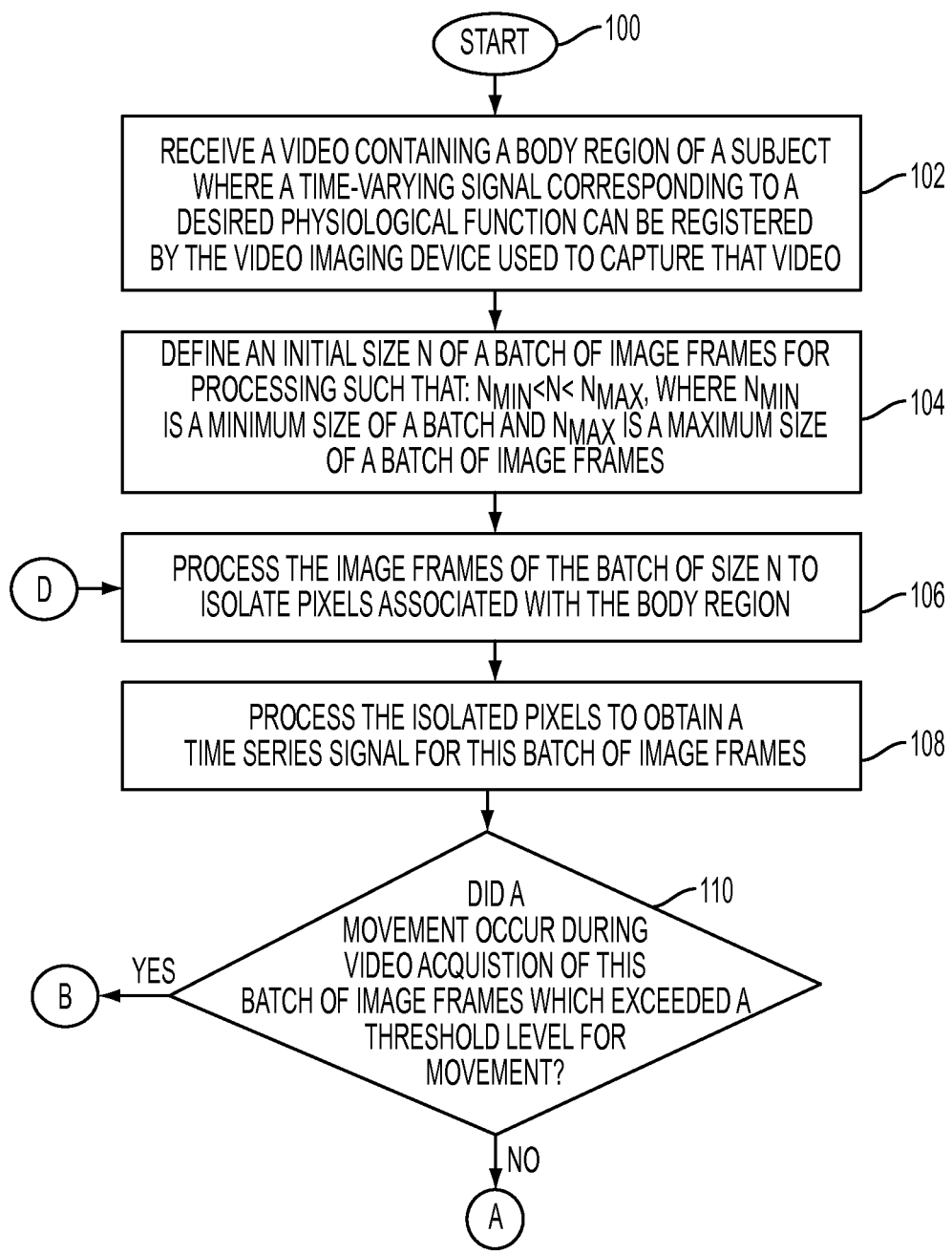
FIG. 1 is a flow diagram of which illustrates one example embodiment of the present method for increasing the accuracy of physiological signals obtained from a video of a subject being monitored for a desired physiological function.

What is disclosed is a system and method for increasing the accuracy of physiological signals obtained from a video of a subject being monitored for a desired physiological function.

Non-Limiting Definitions

A "physiological function" is a respiratory or a cardiac function.

A "subject" refers to a living person or patient being monitored for a physiological function. Although the term "person" or "patient" may be used throughout this text, it should be appreciated that the subject may be something other than a human such as a primate. Such terms are not to be viewed as limiting the scope of the appended claims strictly to human beings.

A "video", as is generally understood, refers to a plurality of time-sequential image frames captured by a video imaging device of a subject being monitored for a physiological function. The video may also contain other components such as, audio, time, frame rate data, and the like. The video is taken of a body region of the subject where a time-varying signal corresponding to the desired physiological function can be registered by the video imaging device used to capture that video.

A "video imaging device" is a single-channel or a multi-channel video capture device, as is generally understood. The video imaging device may be a device with a high frame rate and high spatial resolution such as, for example, a monochrome camera for capturing black/white video, or a color camera for capturing color video. The video imaging device may be a device with thermal, infrared, multi-spectral or hyperspectral sensors. The video imaging device may comprise a hybrid device capable of operating in a conventional video mode with high frame rates and high spatial resolution, and a spectral mode with low frame rates but high spectral resolution. The video imaging device may have a plurality of outputs from which the video can be retrieved or otherwise received on a per-channel basis. The video imaging device may incorporate various components such as memory, one or more storage devices, and processors executing machine readable program instructions for processing and analyzing video in accordance with the teachings hereof. Video imaging devices comprising standard video equipment and those with specialized imaging sensors are available from a wide array of vendors in various streams of commerce.

"Receiving image frames" of a video is intended to be widely construed and includes: retrieving, capturing, acquiring, or otherwise obtaining image frames for processing in accordance with the methods disclosed herein. The image frames can be retrieved from a memory or storage device of the video imaging device, obtained from a remote device over a network, or from a media such as a CDROM or DVD. Image frames may be downloaded from a web-based system or application which makes such video images available for processing. Image frames can also be received from an application such as those which are available for handheld cellular devices and processed on the cellphone or other handheld computing device such as an iPad or tablet.

A "batch of image frames" means a plurality of time-sequential image frames. Batches of image frames are temporally successive, i.e., a next batch of image frames follows the previous batch. In a preferred embodiment, successive batches of image frames significantly overlap each other. In accordance with the teachings hereof, an initial size N of a first batch of image frames is defined such that: $N_{min} \leq N \leq N_{max}$, where $N_{min}$ is a minimum size of a batch of image frames needed to obtain an accurate physiological signal, and $N_{max}$ is a user-defined maximum size of a batch of image frames. For respiratory function assessment, a minimum size of a batch of image frames is preferably not be less than 3 breathing cycles of the subject. For cardiac function assessment, a minimum size of a batch of image frames is preferably not be less than 1 cardiac cycle of the subject. Batches of image frames are processed to obtain a time-series signal for each batch.

A "time-series signal" is a signal, extracted from a batch of image frames, that contains meaningful data that relates to the physiological function for which the subject is being monitored. The time-series signal contains frequency components of interest. Time-series signals can be normalized and may be subjected to pre-filtering to remove undesirable frequencies. A time series signal is generated from a given batch of video image frames by processing pixels in one or more areas of the exposed body region in each of the image frames in the batch. One method for processing pixels involves isolating pixels associated with the body region in the image frame. Pixels can be isolated in the image frames using image processing techniques such as pixel classification based on color, texture, spatial features, spectral information, object identification such as face or thoracic region recognition, pattern recognition, and a user input. Then, averaging pixel values within the isolated areas in each frame for all image frames in the batch. An average is computed of all pixels in each of the isolated areas to obtain a channel average, on a per frame basis. Individual time-series signals can be weighted, as desired. A weighting may be applied over one or more signal segments while other signal segments are not weighted. Methods for weighing segments of a signal are well understood. Time-series signals obtained from batches of image frames are processed to extract a physiological signal.

A "physiological signal" is a signal corresponding to the physiological function for which the subject is being monitored. The physiological signal is extracted from each time-series signal obtained from processing each batch of image frames. Many of the above-incorporated US patent applications teach various aspects of extracting a physiological signal from a time-series signal The physiological signal may be communicated to a display device, a storage device, a hand-held wireless cellular device, or a remote device over a network.

An "exposed body region" of a subject refers to at least a partial view of exposed skin of the subject's body, as seen through the aperture of the video imaging device, where a physiological signal corresponding to the desired physiological function can be registered by the video imaging device. Body regions where a respiratory signal can be registered by the video imaging device are those areas of the subject's body which move due to an expansion and contraction of the chest during respiration. These body regions include the subject's anterior thoracic region, a side view of the subject's thoracic region, and a back region of the subject's dorsal body. Body regions where a cardiac signal can be registered by the video imaging device are those areas of exposed skin where subcutaneous venous or arterial pulsations due to blood flow can be detected.

"Determining whether a movement occurred" means to determine whether movement is likely to have induced motion artifacts into the video image frames comprising that batch. The movement may be caused by the subject, the video imaging device, or when a third party walked between the video imaging device and the subject. Movement may be caused by the environment surrounding the subject such as the patient's bed having moved or the pillow/sheets having shifted, light flicker, and the like. A determination whether movement occurred can be effectuated using a variety of techniques. For example, a motion detector can be utilized to sense the subject and provide a signal when the subject is moving or, conversely, provide a signal when the subject is not moving. A time interval of the image frames associated with movement can be identified accordingly. Movement can also be determined by visual observation by a trained technician tasked with observing the subject during video acquisition. Software tools can be employed to analyze batches of image frames for movement, for instance, by processing pixels in the isolated body region(s) in each of the image frames to determine an amount of change in center pixel locations associated with that area relative to a fixed object in the environment or a fixed position of the subject. Other methods include determining a rate of change of the time series signal of at least one pre-selected channel of the video imaging device; determining whether a derivative of any X or Y locations, orientations, size in the body region in a batch of image frames has changed relative to those same location in a previous batch of image frames; or determining whether a derivative of any X or Y locations in other parts of the subject's body exceed a threshold. Movement can be identified by looking for a change in a shape of the body region in the batch of image frames, i.e., the head turned, an arm moved, etc. A facial recognition algorithm or object tracking method can be utilized for movement determination. Software tools can be configured to send a signal, initiate an alert, or otherwise mark time intervals of image frames when movement was or was not detected.

A "threshold for movement", as used herein, is a level of an amount of movement during video acquisition of a batch of image frames which is used for comparison purposes. The threshold may be based on the physiological function for which the subject is being monitored, i.e., the threshold level set for respiratory function assessment may be entirely different than the threshold set for cardiac function assessment. The threshold level may be based on a type of motion or a source of motion (i.e., by the subject or by the environment). The threshold level may be based on the time of the movement within the batch. The threshold may be set by a user or technician. The threshold for movement may be dynamically adjusted in real-time. Such a dynamic adjustment can be based on, for instance, a signal-to-noise ratio of a power spectrum of the time-series signal obtained from having processed a given batch of pixels, or based on a waveform of a rhythm signal. The threshold may be dynamically adjusted by a user/technician in real-time as the video of the subject is being captured by the video imaging device. It should be appreciated that the threshold set for movement will depend on the application where the teachings hereof find their intended uses. Therefore, a discussion with respect to a particular threshold level is omitted herein. In response to the movement for a given batch of image frames having exceeded the threshold, the time-series signal obtained from that batch may be discarded. Alternatively, an indication is provided that the physiological signal extracted from the time-series signal for this batch may be unreliable and may require further processing. In other embodiments, a motion compensation strategy is applied to reduce the effects of the detected movement. Various other responses to movement exceeding the threshold include, for example, initiating an alert signal that movement is excessive; signaling a medical professional that excessive movement has occurred; changing a frame rate of the video imaging device; swapping the video imaging device for another video camera; moving a position of the video imaging device; and stopping video acquisition altogether.

A "predictive model" is used in predictive analytics to create a statistical model to predict a future behavior or a future result. A predictive model generally comprises a number of variables (i.e., parameters) which have been determined to be predictive of future behavior or results. Multiple predictors are combined into a predictive model which, when subjected to analysis, can forecast future probabilities with an acceptable level of reliability. In predictive modeling, data of past behavior is mined, a predictive model is formulated, parameters of the model are repeatedly revised and validated as additional data becomes available, and the predictive model is used to predict future behavior or results. The predictive model may be as simple as a linear equation or as complex as a neural network. The reader is directed to the texts: "*Applied Predictive Modeling*", Max Kuhn and Kjell Johnson Springer Publishing (September 2013), ISBN-13: 978-1461468486, and "*Applied Linear Regression*", Sanford Weisberg, Wiley Publishing $4^{th}$ Ed. (December 2013), ISBN-13: 978-1118386088, which are incorporated herein in their entirety by reference. In the present method, parameters of the predictive model are repeatedly updated with components of the time-series signals obtained from processing batches of image frames when movement did not exceed a pre-defined threshold level for movement. When it is determined that movement occurred during video acquisition of a given batch of frames exceeding the threshold level set for movement, the latest updated predictive model is then used to generate a "predicted" time-series signal for this particular batch of image frames. The generated predicted time-series signal is then fused with the time-series signal obtained from having processed this batch of image frames. An auto-regressive model or an impulse response is used herein for predictive modeling.

An "auto-regressive model" is a predictive model of a system which specifies that the output depends linearly on values of previous states. Auto-regressive models have been used to describe a wide array of time-varying processes such as those found in nature, economics, etc. Auto-regressive models include auto-regressive moving average (ARMA) models, auto-regressive integrated moving average (ARIMA) models, and auto-regressive fractionally integrated moving average (ARFIMA) models.

An "impulse response function" or simply "impulse response", is a predictive model of a system where an output is generated in response to an input called an "impulse". The response of the function describes the reaction of the system to the impulse. The system's reaction can be a function of time or a function of some other independent variables that parameterize the dynamic behavior of that system.

Fusing" means to combine time-series signal together. Some or all of the time-series signal and the predicted time-series signal may be weighted as desired. Such weights may be as large or as small as desired, including zero. Method for combining (fusing) time-series signals are well established in the signal processing arts. The resulting fused time-series signal may be filtered using, for example, an equiripple band-pass filter, to remove unwanted artifacts.

"Processing" includes the application of any mathematical operation applied to data, according to any specific context, or for any specific purpose as described herein.

Flow Diagram of One Example Embodiment

Reference is now being made to the flow diagram of FIG. 1 which illustrates one example embodiment of the present method for increasing the accuracy of a physiological signal obtained from a video of a subject being monitored for a desired physiological function. Flow processing begins at step 100 and immediately proceeds to step 102.

At step 102, receive a video of a body region of a subject where a time-varying signal corresponding to a desired physiological function is registered by the video imaging device acquiring that video.

At step 104, define an initial size N of a batch of image frames for processing such that $N_{min} \leq N \leq N_{max}$, where $N_{min}$ is a minimum size of a batch of image frames and $N_{max}$ is a maximum size of a batch of image frames.

At step 106, process the batch of image frames to isolate pixels associated with the body region.

At step 108, process the isolated pixels to obtain a time-series signal for this batch of image frames.

At step 110, a determination is made whether a movement occurred during video acquisition of this batch of image frames which exceeded a threshold level of movement.

Figure 2:
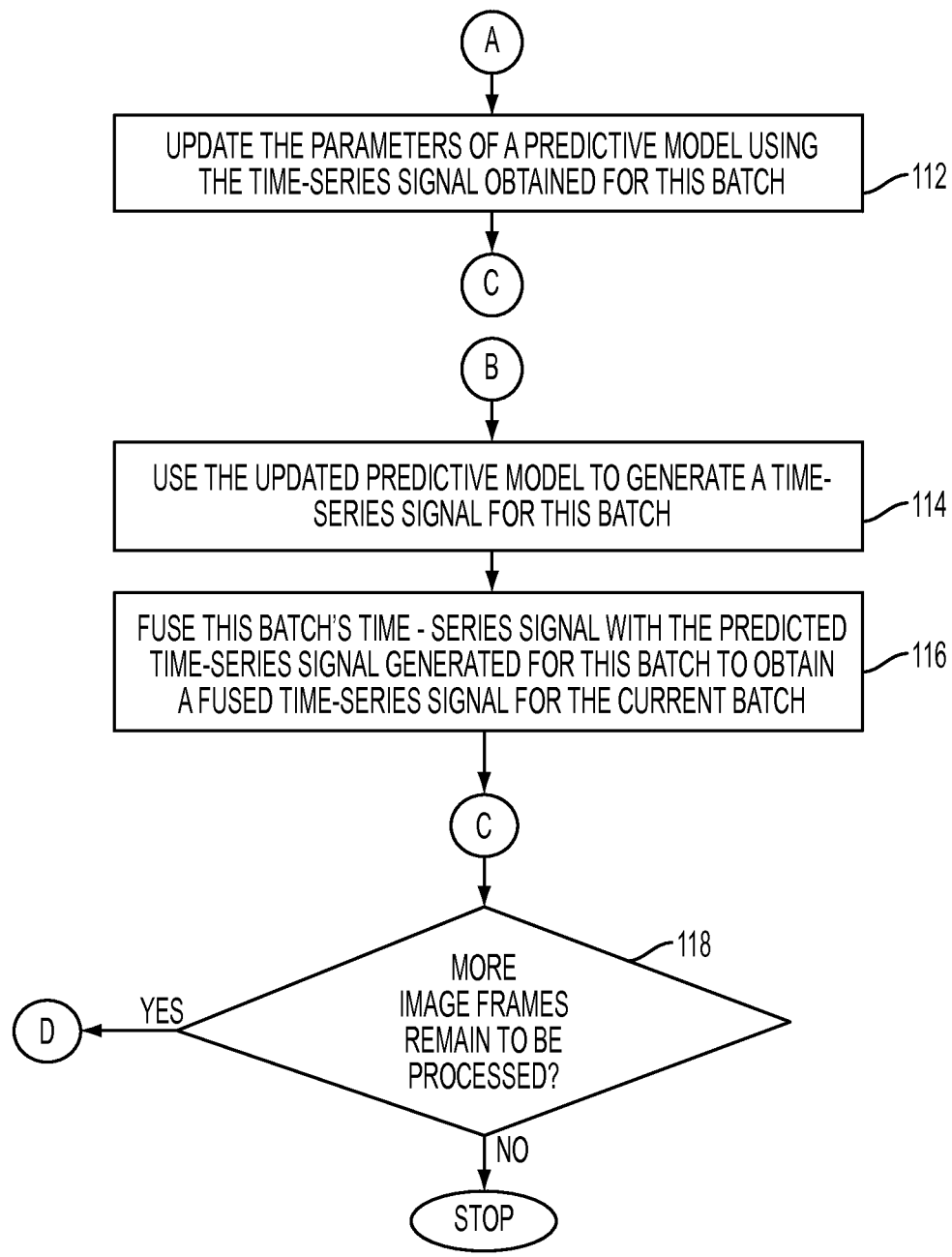
FIG. 2 is a continuation of the flow diagram of FIG. 1 with flow processing continuing with respect to node A.

Reference is now being made to FIG. 2 which is a continuation of the flow diagram of FIG. 1 with flow processing continuing with respect to node A.

If, as a result of the determination in step 110, the movement did not exceed the threshold level set for movement then processing continues with respect to node A wherein, at step 112, update the parameters of a predictive model using the time-series signal obtained for this batch (from step 108). On the other hand, if it is determined that the movement did exceed the threshold level for movement then processing continues with respect to node B wherein, at step 114, use the updated predictive model to generate a predicted time-series signal for the current batch.

At step 116, fuse this batch's time-series signal with the predicted time-series signal generated for this batch (from step 114) to obtain a fused time-series signal for the current batch.

At step 118, a determination is made whether more image frames remain to be processed. If so, then processing continues with respect to node D wherein, at step 106, a next batch of image frames is processed. Processing repeats until no more batches of image frames remain for processing.

In other embodiments, if the movement has exceeded the threshold level set for movement, an alert signal is provided. The alert may take the form of a message displayed on a display device or a sound activated at, for example, a nurse's station or a display of a device. The alert may take the form of a colored or blinking light which provides a visible indication that an alert condition exists. The alert can be a text, audio, and/or video message. The alert signal may be communicated to one or more remote devices over a wired or wireless network. The alert may be sent directly to a handheld wireless cellular device of a medical professional. Thereafter, additional actions would be taken in response to the alert. The above-described method is preferably used for patient monitoring where the image frames of the video are captured by the video imaging device in real-time and processed as they are received to extract a physiological signal corresponding to the desired physiological function.

It should also be appreciated that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Block Diagram of Video Processing System

Figure 3:
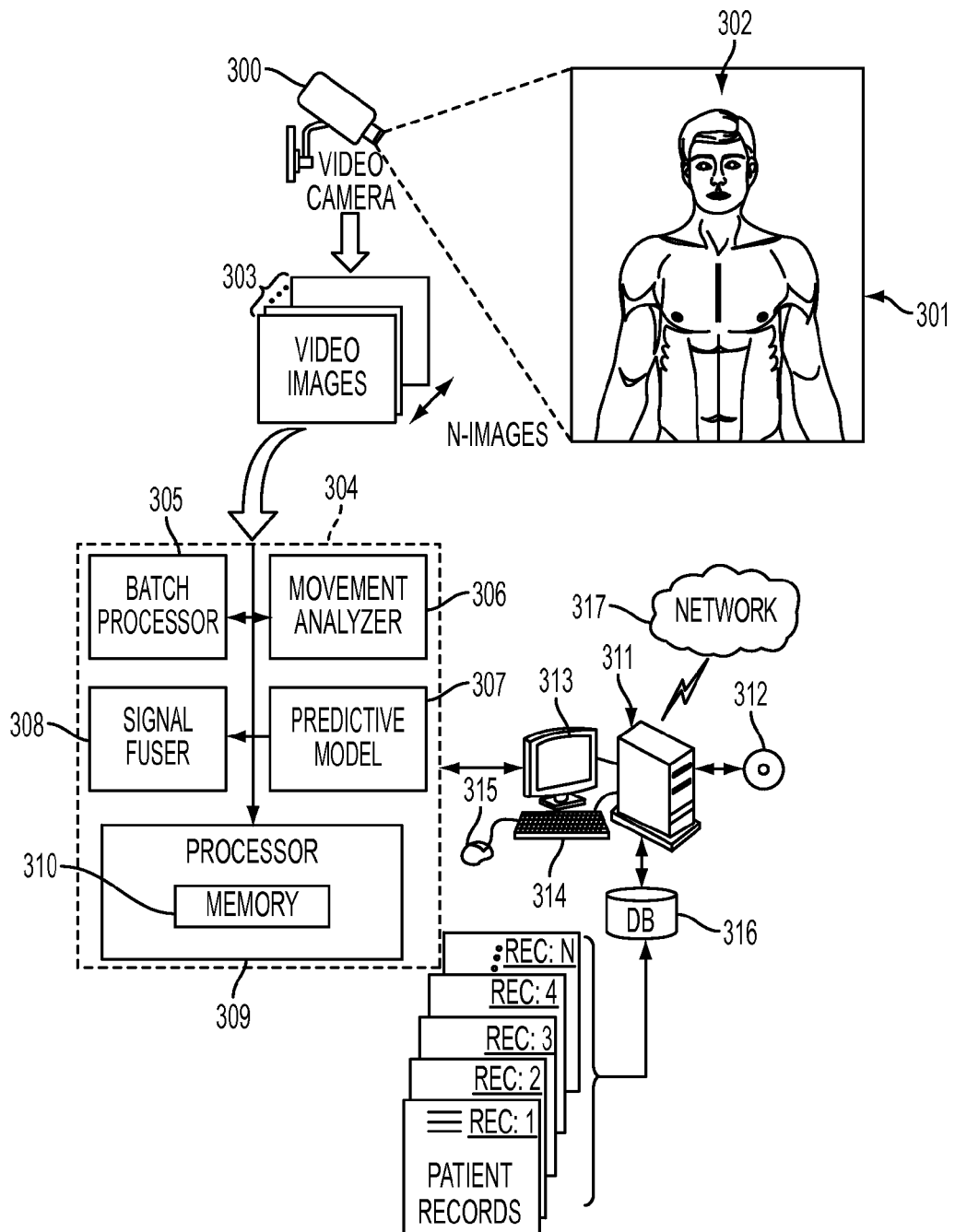
FIG. 3 shows a block diagram of one example video processing system 300 for processing a video in accordance with the embodiment shown and described with respect to the flow diagrams of FIGS. 1-2.

Reference is now being made to FIG. 3 which shows a block diagram of one example video processing system 300 for processing a video in accordance with the embodiment shown and described with respect to the flow diagrams of FIGS. 1-2.

In FIG. 3, video imaging device 300 is shown acquiring a streaming video 301 of an exposed body region of the subject 302. Video images (collectively at 303) are communicated to a Video Processing System 304. Batch Processor 305 receives the defined size N of a batch of image frames from the workstation 311 and continuously processes batches of image frames of size N by isolating pixels associated with the exposed body region in the image frames and then processing the isolated pixels to obtain a time-series signal for each batch. Movement Analyzer 306 process the current batch of image frames and makes a determination whether a movement occurred which exceeded a threshold level which has been set of movement. The determination is provided to Predictive Model Module 307 which, based on the determination, either updates the parameters of the predictive model stored therein or uses the last updated predictive model to generate a predicted time-series signal. Signal Fuser Module 308 receives the time-series signal for the current batch and the predicted time-series signal (when applicable) and proceeds to fuse the two time-series signals together to obtain a fused time-series signal. Processor 309 retrieves machine readable program instructions from Memory 310 and is provided to facilitate the functionality of any of the modules of the Video Processing System 304. Processor 309, operating alone or in conjunction with other processors and memory, can be configured to assist or otherwise perform the functionality of any of the processors and modules of the Video Processing System 304. Processor 309 proceeds to generate a physiological signal from the various time-series signals and communicates the subject's physiological signal to the display device of workstation 311.

A computer case of the workstation 311 houses various components such as a motherboard with a processor and memory, a network card, a video card, a hard drive capable of reading/writing to machine readable media 312 such as a floppy disk, optical disk, CD-ROM, DVD, magnetic tape, and the like, and other software and hardware needed to perform the functionality of a computer workstation. The workstation further includes a display device 313, such as a CRT, LCD, or touchscreen device, for displaying information, video, measurement data, computed values, medical information, results, locations, and the like. A user can view any of that information and make a selection from menu options displayed thereon. A keyboard 314 and mouse 315 effectuate a user input or selection. The workstation has an operating system and other specialized software configured to display alphanumeric values, menus, scroll bars, dials, slideable bars, pull-down options, selectable buttons, and the like, for entering, selecting, modifying, and accepting information needed for processing video image frames in accordance with the teachings hereof. In other embodiments, a user or technician may use the user interface of the workstation to identify areas of interest, set parameters, select image frames and/or regions of images for processing. These selections may be stored/retrieved in a storage devices 312 and 316. Default settings and initial parameters can be retrieved from the storage devices, as needed. Further, a user may adjust the various parameters of the predictive model being employed or dynamically change predictive models in real-time as batches of image frames are processed. The workstation can display the image frames of the streaming video. The workstation implements a database in storage device 316 wherein records are stored, manipulated, and retrieved in response to a query. Such records, in various embodiments, take the form of patient medical histories. Although the database is shown as an external device, the database may be internal to the workstation mounted, for example, on a hard disk housed within the computer case.

Although shown as a desktop computer, it should be appreciated that the workstation can be a laptop, mainframe, or a special purpose computer such as an ASIC, circuit, or the like. The embodiment of the workstation of FIG. 3 is illustrative and may include other functionality known in the arts. Any of the components of the workstation may be placed in communication with the Video Processing System 304 or any devices in communication therewith. Any of the modules and processing units of Video Processing System 304 can be placed in communication with storage devices 312 and 316 and may store/retrieve therefrom data, variables, records, parameters, functions, and/or machine readable/executable program instructions, as needed to perform their intended functions. Each of the modules of the Video Processing System 304 may be placed in communication with one or more remote devices over network 317.

It should be appreciated that some or all of the functionality performed by any of the modules or processing units of Video Processing System 304 can be performed, in whole or in part, by the workstation 311. The workstation may be placed in communication with the video imaging device 300 over network 317. The embodiment of FIG. 3 is illustrative and should not be viewed as limiting the scope of the appended claims strictly to that configuration. Various modules may designate one or more components which may, in turn, comprise software and/or hardware designed to perform the intended function.

Performance Results

The following is an example using the teachings disclosed herein on a video from a healthy subject. Video was captured for a healthy adult using a video imaging device set at 30 frame per second (fps) capture speed for a period of 200 frames. The training batch length was 17 seconds long (512 frames). The sampling period was 0.0333 seconds.

Figure 4:
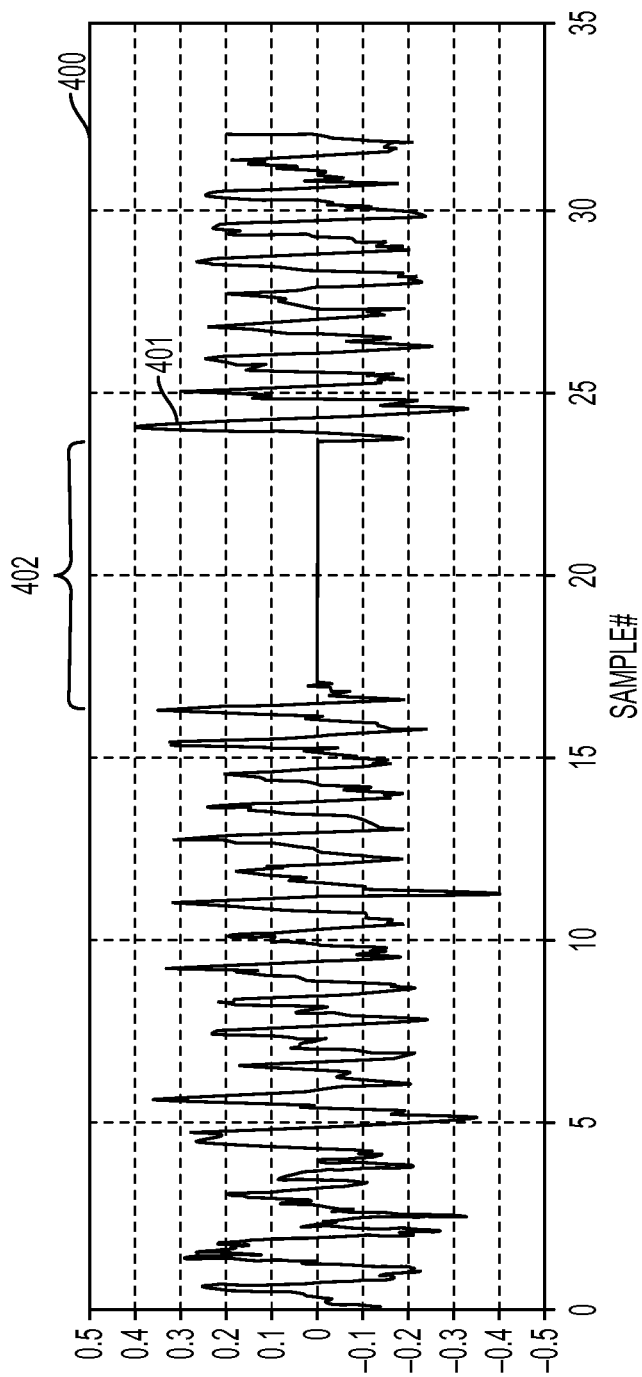
FIG. 4 is a graph of a unfiltered signal obtained from having processed the video image frames.

FIG. 4 is a graph 400 of a unfiltered signal 401 obtained from having processed the video image frames. Signal segment (at 402) is when a movement occurred which exceeded the threshold level.

Figure 5:
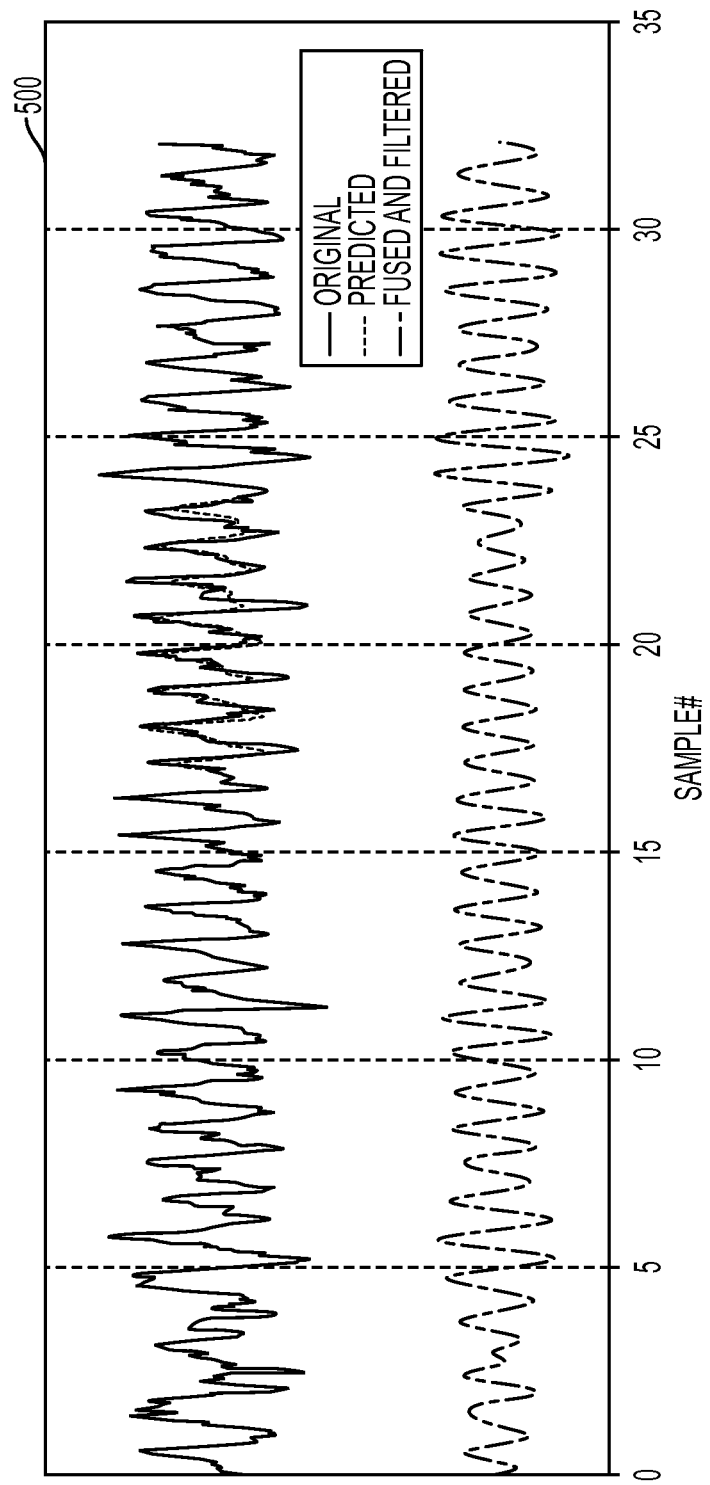
FIG. 5 is a graph of the unfiltered signal of FIG. 4 overlaid with a predicted signal.

FIG. 5 is a graph 500 of the unfiltered signal of FIG. 4 overlaid with a predicted signal. The fused & filtered signal is shown in the same graph.

Figure 6:
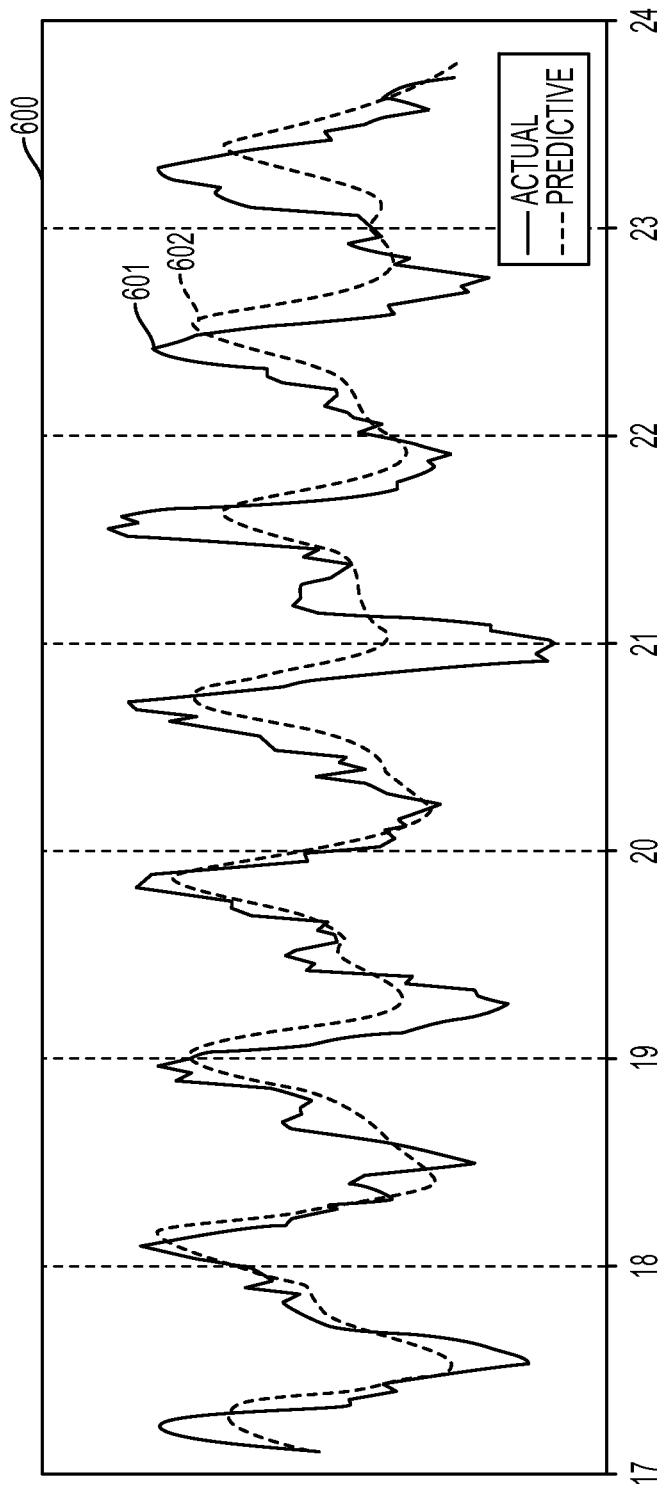
FIG. 6 is a graph of the predicted signal with an actual signal to show correlation.

FIG. 6 is a graph 600 of the actual signal (solid line at 601) of the subject in the video overlaid with the predicted signal (dashed line at 602). The predicted signal appears to correlate with the actual signal. It should be noted that we start losing phase and signal strength as the forecasting horizon becomes long. Final filtering was carried out with an equiripple bandpass filter.

Various Embodiments

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture which may be shipped, sold, leased, or otherwise provided separately either alone or as part of a product suite or a service.

It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are each hereby incorporated by reference in their entirety.

What is claimed is:

1. A method for increasing the accuracy of physiological signals obtained from a video of a subject being monitored for a desired physiological function, the method comprising:
   receiving image frames of a video captured by a video imaging device of a subject being monitored for a desired physiological function, said image frames being acquired of at least a portion of an exposed body region of said subject where a physiological signal corresponding to said desired physiological function can be registered by said video imaging device;
   defining a size N of a batch of image frames such that $N_{min} \leq N \leq N_{max}$, where $N_{min}$ is a minimum size of a batch of image frames and $N_{max}$ is a maximum size of a batch of image frames; and
   for each batch of image frames of size N:
      processing the current batch of image frames to isolate pixels associated with said body region;
      processing said isolated pixels to obtain a time-series signal for this batch;
      determining whether a movement occurred during video acquisition of this batch of image frames; and
      in response to said movement being below a predetermined threshold level, updating the parameters of a predictive model using said obtained time-series signal, otherwise:
         using said updated predictive model to generate a predicted time-series signal for the current batch; and
         fusing said time-series signal with said predicted time-series signal to obtain a fused time-series signal for the current batch.

2. The method of claim 1, where said video imaging device is any of: a color video camera, a monochrome video camera, an infrared video camera, a multispectral video imaging device, and a hyperspectral video camera.

3. The method of claim 1, wherein pixels associated within said body region are isolated in said image frames using any of: pixel classification based on color, texture, spatial features, spectral information, object identification, pattern recognition, and a user input.

4. The method of claim 1, wherein determining whether said movement occurred comprises any of:
   determining a rate of change of said time series signal of at least one pre-selected channel of said video camera;
   determining whether a derivative of any X or Y locations, orientations, size in said region of interest has changed relative to a previous time; and
   determining whether a derivative of any X or Y locations in other parts of the subject's body exceed a pre-defined threshold.

5. The method of claim 1, wherein said predictive model comprises any of: an auto-regressive model, and an impulse response function.

6. The method of claim 1, wherein said threshold level of movement is based upon any of:
   said physiological function for which said subject is being monitored;
   a type of motion detected in said batch of image frames;
   a source of said motion;
   a time when said motion occurred; and
   a user input.

7. The method of claim 1, wherein, in advance of fusing, further comprising any of:
  weighting at least one segment of said time-series signal; and
  weighting at least one segment of said predicted time-series signal.

8. The method of claim 1, wherein, in response to said movement exceeding said threshold, further comprising any of:
  providing an indication that a physiological signal extracted from said time-series signal for said current batch may be unreliable; and
  adjusting said size of said batch of image frames.

9. The method of claim 1, wherein, in response to said movement exceeding said threshold level, further comprising any of:
  initiating an alert signal;
  signaling a medical professional;
  changing a frame rate of said video imaging device;
  moving a position of said video imaging device;
  swapping said video imaging device for another video camera; and
  stopping video acquisition of said subject.

10. The method of claim 1, further comprising filtering said fused time-series signal to remove artifacts introduced by said fusing.

11. The method of claim 1, further comprising processing said time-series signal to obtain a physiological signal which corresponds to said physiological function.

12. The method of claim 1, further comprising dynamically adjusting said threshold level of movement based on any of: a signal-to-noise ratio of a power spectrum of said time-series signal, a waveform of a rhythm signal, and a user input.

13. The method of claim 1, wherein said video is a streaming video and said video image frames are processed in real-time as they are received.

14. A system for increasing the accuracy of physiological signals obtained from a video of a subject being monitored for a desired physiological function, the system comprising:
  a memory and a storage device; and
  a processor in communication with said memory and storage device, said processor executing machine readable instructions for performing:
    receiving image frames of a video captured by a video imaging device of a subject being monitored for a desired physiological function, said image frames being acquired of at least a portion of an exposed body region of said subject where a physiological signal corresponding to said desired physiological function can be registered by said video imaging device;
    defining a size N of a batch of image frames such that $N_{min} \leq N \leq N_{max}$, where $N_{min}$ is a minimum size of a batch of image frames and $N_{max}$ is a maximum size of a batch of image frames; and
    for each batch of image frames of size N:
      processing the current batch of image frames to isolate pixels associated with said body region;
      processing said isolated pixels to obtain a time-series signal for this batch;
      determining whether a movement occurred during video acquisition of this batch of image frames; and
      in response to said movement being below a predetermined threshold level, updating the parameters of a predictive model using said obtained time-series signal, otherwise:
        using said updated predictive model to generate a predicted time-series signal for the current batch; and
        fusing said time-series signal with said predicted time-series signal to obtain a fused time-series signal for the current batch.

15. The system of claim 14, where said video imaging device is any of: a color video camera, a monochrome video camera, an infrared video camera, a multispectral video imaging device, and a hyperspectral video camera.

16. The system of claim 14, wherein pixels associated within said body region are isolated in said image frames using any of: pixel classification based on color, texture, spatial features, spectral information, object identification, pattern recognition, and a user input.

17. The system of claim 14, wherein determining whether said movement occurred comprises any of:
  determining a rate of change of said time series signal of at least one pre-selected channel of said video camera;
  determining whether a derivative of any X or Y locations, orientations, size in said region of interest has changed relative to a previous time; and
  determining whether a derivative of any X or Y locations in other parts of the subject's body exceed a pre-defined threshold.

18. The system of claim 14, wherein said predictive model comprises any of: an auto-regressive model, and an impulse response function.

19. The system of claim 14, wherein said threshold level of movement is based upon any of:
  said physiological function for which said subject is being monitored;
  a type of motion detected in said batch of image frames;
  a source of said motion;
  a time when said motion occurred; and
  a user input.

20. The system of claim 14, wherein, in advance of fusing, further comprising any of:
  weighting at least one segment of said time-series signal; and
  weighting at least one segment of said predicted time-series signal.

21. The system of claim 14, wherein, in response to said movement exceeding said threshold, further comprising any of:
  providing an indication that a physiological signal extracted from said time-series signal for said current batch may be unreliable; and
  adjusting said size of said batch of image frames.

22. The system of claim 14, wherein, in response to said movement exceeding said threshold level, further comprising any of:
  initiating an alert signal;
  signaling a medical professional;
  changing a frame rate of said video imaging device;
  moving a position of said video imaging device;
  swapping said video imaging device for another video camera; and
  stopping video acquisition of said subject.

23. The system of claim 14, further comprising filtering said fused time-series signal to remove artifacts introduced by said fusing.

24. The system of claim 14, further comprising processing said time-series signal to obtain a physiological signal which corresponds to said physiological function.

25. The system of claim 14, further comprising dynamically adjusting said threshold level of movement based on any of: a signal-to-noise ratio of a power spectrum of said time-series signal, a waveform of a rhythm signal, and a user input.

* * * * *